United States Patent
Cook et al.

(10) Patent No.: US 6,350,716 B1
(45) Date of Patent: Feb. 26, 2002

(54) CATALYST AND PROCESS FOR THE OXIDATION OF ETHANE AND/OR ETHYLENE

(75) Inventors: John Cook, Hull; Brian Ellis, Lower Sunbury; Philip Howard, East Yorkshire; Michael David Jones, Beverley; Simon James Kitchen, Hillam, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/665,905

(22) Filed: Sep. 20, 2000

Related U.S. Application Data

(63) Continuation of application No. PCT/GB99/00996, filed on Mar. 31, 1999.

(30) Foreign Application Priority Data

Apr. 2, 1998 (GB) ............................................. 9807142

(51) Int. Cl.⁷ .............................. B01J 23/00; B01J 21/02
(52) U.S. Cl. ....................... 502/300; 502/202; 502/204; 502/215; 502/305; 502/355
(58) Field of Search .......................... 502/202, 204–215, 502/305–355

(56) References Cited

U.S. PATENT DOCUMENTS

| | | | | |
|---|---|---|---|---|
| 2,885,409 A | | 5/1959 | Ryder ...................... 260/346.8 |
| 4,250,346 A | * | 2/1981 | Young et al. ................ 585/658 |
| 4,524,236 A | * | 6/1985 | McCain ...................... 585/658 |
| 4,568,790 A | * | 2/1986 | McCain ...................... 585/658 |
| 4,596,787 A | | 6/1986 | Manyik et al. ............. 502/312 |
| 4,797,381 A | * | 1/1989 | Bartek et al. .............. 502/312 |
| 4,808,563 A | * | 2/1989 | Velenyi ...................... 502/312 |
| 5,173,468 A | * | 12/1992 | Boehning et al. .......... 502/312 |
| 5,300,682 A | | 4/1994 | Blum et al. ............... 562/512.2 |
| 5,498,588 A | * | 3/1996 | Brazdil et al. .............. 502/312 |
| 5,625,084 A | | 4/1997 | Pitchai et al. .............. 549/536 |
| 5,637,546 A | * | 6/1997 | Tenten et al. .............. 502/312 |
| 5,750,777 A | | 5/1998 | Aubry et al. ............... 562/549 |
| 5,994,580 A | * | 11/1999 | Takahashi et al. .......... 502/312 |
| 6,013,597 A | * | 1/2000 | Karim et al. ............... 502/209 |
| 6,043,185 A | * | 3/2000 | Cirjak et al. ................ 502/312 |

FOREIGN PATENT DOCUMENTS

| | | |
|---|---|---|
| CH | 419 067 | 2/1967 |
| DE | 196 20 542 A1 | 11/1997 |
| DE | 196 30 832 A1 | 2/1998 |
| EP | 0 006 248 A1 | 1/1980 |
| EP | 0 043 100 A1 | 1/1982 |
| EP | 0 166 438 | 1/1986 |
| EP | 0 407 091 A1 | 1/1991 |
| EP | 0 719 756 A1 | 7/1996 |
| WO | 96/37297 | 11/1996 |
| WO | 98/05620 | 2/1998 |
| WO | 98/47850 | 10/1998 |
| WO | 99/20592 | 4/1999 |

OTHER PUBLICATIONS

Chemical Abstract No. 1998:59329 "Manufacture of acetic acid by using . . . ," Koyasu et al (Jan. 1998).

* cited by examiner

*Primary Examiner*—Mark L. Bell
*Assistant Examiner*—Patricia L. Hailey
(74) *Attorney, Agent, or Firm*—Nixon & Vanderhye

(57) ABSTRACT

A catalyst composition for the selective oxidation of ethane and/or ethylene to acetic acid which composition comprises in combination with oxygen the elements: $Mo_a.W_b.Ag_c.Ir_d.X_e.Y_f$ (I) wherein X is the elements Nb and V; Y is one or more elements selected from the group consisting of: Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd; a, b, c, d, e and f represent the gram atom ratios of the elements such that $0<a\leq1$, $0\leq b\leq1$ and $a+b=1$; $0<(c+d)\leq0.1$; $0<e\leq2$; and $0\leq f\leq2$. The catalyst composition may be used in the production of acetic acid and in an integrated process for the production of acetic acid and/or vinyl acetate.

29 Claims, No Drawings

CATALYST AND PROCESS FOR THE OXIDATION OF ETHANE AND/OR ETHYLENE

This is a continuation of PCT application No. PCT/GB99/00996, filed Mar. 31, 1999, the entire content of which is hereby incorporated by reference in this application.

The present invention relates to a catalyst for the oxidation of ethane and/or ethylene to acetic acid and to a process for the production of acetic acid utilising the aforesaid catalyst.

Catalysts and processes for the production of acetic acid by the oxidation of ethane and ethylene are known in the art from, for example, U.S. Pat. No. 4,250,346; EP-A-0407091; DE-A-19620542; and DE-A-19630832.

U.S. Pat. No. 4,250,346 discloses the oxidative dehydrogenation of ethane to ethylene in a gas phase reaction at relatively high levels of conversion, selectivity and productivity at a temperature less than 500° C. using as catalyst a composition comprising the elements molybdenum, X and Y in the ratio $$Mo_aX_bY_c$$

wherein

X is Cr, Mn, Nb, Ta, Ti, V and/or W, and preferably Mn, Nb, V and/or W

Y is Bi, Ce, Co, Cu, Fe, K, Mg, Ni, P, Pb, Sb, Si, Sn, Tl and/or U, and preferably Sb, Ce and/or U, a is 1, b is 0.05 to 1.0 and c is 0 to 2, and preferably 0.05 to 1.0, with the proviso that the total value of c for Co, Ni and/or Fe is less than 0.5.

EP-A-0407091 discloses a process for the production from gaseous ethane and/or ethylene of a product comprising ethylene and/or acetic acid, by contacting the ethane and/or ethylene and a molecular oxygen-containing gas at elevated temperature with a calcined molybdenum-containing ethane oxidative dehydrogenation catalyst composition characterised in that molybdenum in the oxidative dehydrogenation catalyst composition is replaced in whole or in part by either rhenium or a combination of rhenium and tungsten.

Also disclosed in EP-A-0407091 is a catalyst comprising the elements A, X and Y in combination with oxygen, the gram-atom ratios of the elements A:X:Y being a:b:c, wherein $A=Mo_dR_eW_f$, X=Cr, Mn, Nb, Ta, Ti, V and/or W, and preferably Mn, Nb, V and/or W, Y=Bi, Ce, Co, Cu, Fe, K, Mg, Ni, P, Pb, Sb, Si, Sn, Tl and/or U, and preferably Sb, Ce and/or U, a=1, b=0 to 2, preferably 0.05 to 1.0, c=0 to 2, preferably 0.001 to 1.0, and more preferably 0.05 to 1.0 with the proviso that the total value of c for Co, Ni, and/or Fe is less than 0.5, d+e+f=a, d is either zero or greater than zero, e is greater than zero, and f is either zero or greater than zero.

DE-A-19620542 discloses a catalyst for the selective oxidation of ethane and/or ethylene to acetic acid containing the elements Mo, Pd, Re, X and Y in the gram atom ratios a:b:c:d:e in combination with oxygen $$Mo_aPd_bRe_cX_dY_e \qquad (I)$$

where the symbols X, Y have the following signification:

X=Cr, Mn, Nb, B, Ta, Ti, V and/or W

Y=Bi, Ce, Co, Cu, Te, Fe, Li, K, Na, Rb, Be, Mg, Ca, Sr, Ba, Ni, P, Pb, Sb, Si, Sn, Tl and/or U;

the indices a, b, c, d and e stand for the gram atom ratios of the corresponding elements, where a=1, b>0, c>0, d=0.05 to 2 and e=0 to 3. Also disclosed in DE-A-19620542 is a process for the selective production of acetic acid from a gaseous charge of ethane, ethylene or mixtures thereof in addition to oxygen by bringing the gaseous charge into contact with a catalyst of the formula (I).

Finally, DE-A-19630832 discloses a catalyst for the selective oxidation of ethane, ethylene or mixtures thereof as well as oxygen, containing the elements Mo, Pd, X and Y in the gram ratios a:b:c:d in combination with oxygen $$Mo_aPd_bX_cY_d \qquad (I)$$

where the symbols X, Y have the following signification:

X stands for one or more of the elements selected from the group Cr, Mn, Nb, Ta, Ti, V and W;

Y stands for one or more of the elements selected from the group B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl, and U;

the indices a, b, c, d stand for the gram atom ratios of the corresponding elements, where a=1; b>0; c>0 and d=0–2. Also disclosed in DE-A-19630832 is a process for the selective production of acetic acid from a gaseous charge of ethane; ethylene or mixtures thereof in addition to oxygen by contacting the gaseous charge with a catalyst of the formula (I).

International patent publication WO 98/47850 published after the priority date of the present application relates to a process and catalyst for preparing acetic acid by catalytic oxidation of ethane. The catalyst used has the formula $W_aX_bY_cZ_d$ in which X stand for one or more elements selected from the group Pd, Pt, Ag and/or Au; Y stands for one or more elements selected from the group V, Nb, Cr, Mn, Fe, Sn, Sb, Cu, Zn, U, Ni and/or Bi; Z stands for one or more elements selected from the group Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and/or Te in the formula a=1, b is greater than 0, c is greater than 0 and d is a number from 0 to 2. Tungsten is thus an essential component of the catalyst.

U.S. Pat. No. 5,750,777 (equivalent to EP-A-719756) relates to production of acetic acid by oxidation of ethane in the presence of a catalyst in which the active phase comprises vanadium, titanium, molybdenum, phosphorus and oxygen which includes a dopant from the following elements: K, Rb, Cs, Ca, Mg, Zr, Hf, Nb, Ta, Cr, W, Mn, Re, Fe, Ru, Os, Rh, Ir, Ni, Pd, Cu, Ag, Zn, Cd, Ti, Si, Ge, Sn, As, Sb, Bi, Ga and the rare earths. However, there are no specific examples containing silver or iridium.

U.S. Pat. No. 4,568,790 relates to a process for the low temperature catalytic oxydehydrogenation of ethane to ethylene in a gas phase using a catalyst having a calcined composition of $Mo_aV_bNb_cSb_d$ wherein a=0.5 to 0.9, b=0.1 to 0.4, c=0.001 to 0.2 and d=0.001 to 0.1.

U.S. Pat. No. 4,596,787 relates to a process for preparing a supported catalyst for the low temperature oxydehydrogenation of ethane to ethylene in a gas phase, including catalysts having a calcined composition containing $Mo_aV_b$-$Nb_cSb_dX_e$ wherein X=nothing or at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and W, a=0.5 to 0.9, b=0.1 to 0.4, c=0.001 to 0.2, d=0.001 to 0.1 and e=0.001 to 1.0 for X equal to at least one element and e=0 for X=0.

There remains a need for a catalyst for the selective oxidation of ethane and/or ethylene to acetic acid and a process for the selective production of acetic acid employing the catalyst. We have found that oxidation catalysts employing silver and/or iridium as an essential component can fulfill the need for a selective oxidation catalyst and process employing same.

Accordingly, the present invention provides a catalyst composition for the selective oxidation of ethane and/or ethylene to acetic acid which composition comprises in combination with oxygen the elements:

$$Mo_a \cdot W_b \cdot Ag_c \cdot Ir_d \cdot X_e \cdot Y_f \qquad (I)$$

wherein X is the elements Nb and V;

Y is one or more elements selected from the group consisting of:
Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd;

a, b, c, d, e and f represent the gram atom ratios of the elements such that
$0 < a \leq 1$, $0 \leq b < 1$ and $a+b=1$;
$0 < (c+d) \leq 0.1$;
$0 < e \leq 2$; and
$0 \leq f \leq 2$.

Catalysts embraced within the formula (I) include:

$Mo_a \cdot W_b \cdot Ag_c \cdot X_e \cdot Y_f$ $Mo_a \cdot W_b \cdot Ir_d \cdot X_e \cdot Y_f$ $Mo_a \cdot W_b \cdot [Ag+Ir]_{c+d} \cdot X_e \cdot Y_f$ $Mo_a \cdot Ag_c \cdot X_e \cdot Y_f$ $Mo_a \cdot Ir_d \cdot X_e \cdot Y_f$ $Mo_a \cdot [Ag+Ir]_{c+d} \cdot X_e \cdot Y_f$ $[Mo+W]_{a+b} \cdot Ag_e \cdot X_e \cdot Y_f$ $[Mo+W]_{a+b} \cdot Ir_d \cdot X_e \cdot Y_f$ $[Mo+W]_{a+b} \cdot [Ag+Ir]_{c+d} \cdot X_e \cdot Y_f$ Examples of suitable catalysts having the formula (I) include:

(i) $Mo_{0.37} \cdot Ag_{0.01} \cdot Re_{0.25} \cdot V_{0.26} \cdot Nb_{0.07} \cdot Sb_{0.03} \cdot Ca_{0.02} \cdot Oy'$ which renormalised on the basis of Mo is the same as $Mo_{1.00} \cdot Re_{0.069} \cdot V_{0.72} \cdot Nb_{0.25} \cdot Sb_{0.08} \cdot Ca_{0.03} \cdot Ag_{0.028}Oy$;

(ii) $Mo_{0.37} \cdot Ir_{0.01} \cdot Re_{0.25} \cdot V_{0.26} \cdot Nb_{0.07} \cdot Sb_{0.03} \cdot Ca_{0.02} \cdot Oy'$ which renormalised on the basis of Mo is the same as $Mo_{1.00} \cdot Re_{0.69} \cdot V_{0.72} \cdot Nb_{0.25} \cdot Sb_{0.08} \cdot Ca_{0.03} \cdot Ir_{0.028}Oy$;

(iii) $Mo_{1.00} \cdot V_{0.25} \cdot Nb_{0.12} \cdot Ag_{0.014}Oy$; and (iv) $Mo_{1.00} \cdot V_{0.25} \cdot Nb_{0.12} \cdot Ag_{0.000028} \cdot Ir_{0.0000018}Oy$.

wherein y' and y are numbers which satisfy the valencies of the elements in the composition for oxygen.

An advantage of catalyst compositions according to the present invention is that they can be more active and selective in converting ethane and/or ethylene to acetic acid.

Preferably, silver and/or iridium is present in an effective amount such that c+d is at least $10^{-6}$. Preferably, c and d are such that $(c+d) \leq 0.05$. Silver is more effective than iridium. Preferably, more silver is present than iridium on a gram atom basis. Preferably, c and d are such that c is at least 10 times greater than d.

Preferably, e is at least 0.05, more preferably e is at least 0.2. Preferably, e is no greater than 0.5. Yet more preferably, e is such that $0.05 \leq e \leq 0.5$. Still more preferably, e is such that $0.2 \leq e \leq 0.5$.

Preferably, f is at least $10^{-6}$. Preferably, f is no greater than 0.2. Yet more preferably, f is such that $10^{-6} \leq f \leq 0.2$.

Preferably, Y is at least one element selected from the group consisting of Cu, Pd, Pt, Re, Ru and Sb.

Preferably, a is at least 0.1. More preferably, a is at least 0.5. Preferably, b is no greater than 0.9.

The catalyst compositions may be prepared by any of the methods conventionally employed for the preparation of catalysts. Suitably the catalyst may be prepared from a solution of soluble compounds and/or complexes and/or compounds of each of the metals. The solution is preferably an aqueous system having a pH in the range from 1 to 12, preferably from 2 to 8, at a temperature of from 20° to 100° C.

Generally, a mixture of compounds containing the elements is prepared by dissolving sufficient quantities of soluble compounds and dispersing any insoluble compounds so as to provide a desired gram-atom ratio of the elements in the catalyst composition. The catalyst composition may then be prepared by removing the solvent from the mixture. The catalyst may be calcined by heating to a temperature of from 200 to 550° C., suitably in air or oxygen, for a period of from 1 minute to 24 hours. Preferably, the air or oxygen is slowly flowing.

The catalyst may be used unsupported or supported. Suitable supports include silica, alumina, zirconia, titania, silicon carbide and mixtures of two or more thereof.

Further details of a suitable method for preparing a catalyst composition may be found in, for example, EP-A-0166438.

The catalyst may be used in the form of a fixed or a fluidised bed.

In another embodiment the present invention provides a process for the production of acetic acid from a gaseous mixture comprising ethane and/or ethylene which process comprises contacting the gaseous mixture with a molecular oxygen-containing gas at elevated temperature in the presence of a catalyst composition as hereinbefore described.

The feed gas comprises ethane and/or ethylene, preferably ethane.

Ethane and/or ethylene may be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkenes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane and/or ethylene and the molecular oxygen-containing gas, water (steam) because this can improve the selectivity to acetic acid.

The elevated temperature may suitably be in the range from 200 to 500° C., preferably from 200 to 400° C.

The pressure may suitably be atmospheric or superatmospheric, for example in the range from 1 to 50 bar, preferably from 1 to 30 bar.

The catalyst composition is preferably calcined before use in the process of the invention. Calcination may suitably be achieved by heating at a temperature suitably in the range from 250 to 500° C. in the presence of an oxygen-containing gas, for example air.

Operating conditions and other information applicable to the performance of the invention may be found in the aforesaid prior art, for example U.S. Pat. No. 4,250,346.

In a preferred embodiment, the oxidation catalyst of the present invention may be used in an integrated process for the production of acetic acid and/or vinyl acetate such as that described, for example, in International patent publication WO 98/05620, the contents of which are incorporated herein by reference. Thus, according to this embodiment, there is provided an integrated process for the production of acetic acid and/or vinyl acetate which comprises the steps:

(a) contacting in a first reaction zone a gaseous feedstock comprising ethylene and/or ethane and optionally steam with a molecular oxygen-containing gas in the presence of a catalyst active for the oxidation of ethylene to acetic acid and/or ethane to acetic acid and ethylene as hereinbefore described, to produce a first product stream comprising acetic acid, water and ethylene (either as unreacted ethylene and/or as co-produced ethylene) and optionally also ethane, carbon monoxide, carbon dioxide and/or nitrogen; and (b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene.

Preferably the integrated process comprises the further steps of:

(c) separating the product stream from step (b) by distillation into an overhead azeotrope fraction comprising vinyl acetate and water and a base fraction comprising acetic acid; and (d) either (i) recovering acetic acid from the base fraction separated in step (c) and optionally recycling the azeotrope fraction separated in step (c) after partial or complete separation of the water therefrom to step (c), or (ii) recovering vinyl acetate from the azeotrope fraction separated in step (c) and optionally recycling the base fraction separated in step (c) to step (b), or (iii) recovering acetic acid from the base fraction separated in step (c) and recovering vinyl acetate from the overhead azeotrope fraction recovered in step (c).

The catalyst and processes of the present invention will now be further illustrated by reference to the following Examples.

CATALYST PREPARATION

In the following examples and comparative examples, the nominal compositions of the catalysts are given. These were calculated from the amounts of reagents used in the preparations of the catalysts.

Comparative Examples A to G.

The following comparative examples A to G are not examples according to the present invention, because they do not conform to the essential composition of such a catalyst principally in the respect that they do not contain silver and/or iridium. They are included only for the purpose of comparison.

Comparative Example A. ($Mo_{1.00}V_{0.25}Nb_{0.12}O_y$)

A solution A was prepared by dissolving 12.71 g ammonium molybdate in 50 ml water heated to 70° C. A second solution B was prepared by dissolving 2.11 g ammonium vanadate in 70 ml water heated to 70° C. Another solution C was prepared by dissolving 2.43 g niobium chloride and 2.02 g oxalic acid in 50 ml water heated to 70° C. Next, solution C was added to solution B and the resulting mixture heated at 70° C. for 15 minutes. Solution A was then added and the final mixture heated at 70° C. for 15 minutes, before evaporating the mixture to dryness over not more than 2 hours. The resulting catalyst cake was ground then calcined in static air in an oven at 350° C. for 5 hours. The nominal composition of the catalyst was thus $Mo_{1.00}V_{0.25}Nb_{0.12}O_y$.

Comparative Example B ($Mo_{1.00}V_{0.25}O_y$)

As for comparative example A except that no solution C was prepared. The nominal composition of the catalyst was thus $Mo_{1.00}V_{0.25}O_y$.

Comparative Example C
($Mo_{1.00}V_{0.25}Nb_{0.12}Pd_{0.01}O_y$)

As for comparative example A except that 0.23 g Pd acetate was added in the preparation of solution A. The nominal composition of the catalyst was thus $Mo_{1.00}V_{0.25}Nb_{0.12}Pd_{0.01}O_y$.

Comparative Example D
($Mo_{1.00}V_{0.25}Nb_{0.12}Ru_{0.01}O_y$)

As for comparative example A except that 0.36 g of ammonium Ru hexachloride was added in the preparation of solution A. The nominal composition of the catalyst was thus $Mo_{1.00}V_{0.25}Nb_{0.12}Ru_{0.01}O_y$.

Comparative Example E
($Mo_{1.00}V_{0.25}Nb_{0.12}Rh_{0.01}O_y$)

As for comparative example A except that 0.15 g of Rh (III) hydroxide was added in the preparation of solution A. The nominal composition of the catalyst was thus $Mo_{1.00}V_{0.25}Nb_{0.12}Rh_{0.01}O_y$.

Comparative Example F
($Mo_{1.00}Re_{0.69}V_{0.72}Nb_{0.25}Sb_{0.08}Ca_{0.03}O_y$)

Solution A was prepared by dissolving 9.53 g ammonium molybdate and 10.06 g ammonium rhenate in 50 ml water heated to 70° C. Solution B was prepared by dissolving 4.56 g ammonium vanadate in 70 ml water heated to 70° C. Solution C was prepared by dissolving 3.65 g niobium chloride, 1.34 g antimony acetate, 0.26 g calcium nitrate and 4.05 g oxalic acid in 50 ml water heated to 70° C. The rest of the procedure was as in comparative example A. The nominal composition of the catalyst was thus $Mo_{1.00}Re_{0.69}V_{0.72}Nb_{0.25}Sb_{0.08}Ca_{0.03}O_y$.

Comparative Example G
($Mo_{1.00}Re_{0.69}V_{0.72}Nb_{0.25}Sb_{0.08}Ca_{0.03}Pd_{0.011}O_y$).

Solution A was prepared by dissolving 4.76 g ammonium molybdate, 5.03 g ammonium rhenate and 0.06 g palladium acetate in 50 ml water heated to 70° C. Solution B was prepared by dissolving 2.28 g ammonium vanadate in 70 ml water heated to 70° C. Solution C was prepared by dissolving 1.82 g niobium chloride, 0.67 g antimony acetate, 0.26 g calcium nitrate and 1.97 g oxalic acid in 50 ml water heated to 70° C. The rest of the procedure was as in comparative example A. The nominal composition of the catalyst was thus $Mo_{1.00}Re_{0.69}V_{0.72}Nb_{0.25}Sb_{0.08}Ca_{0.03}Pd_{0.011}O_y$.

Examples according to the Present Invention

Example I ($Mo_{1.00}Re_{0.69}V_{0.72}Nb_{0.25}Sb_{0.08}Ca_{0.03}Ag_{0.028}O_y$)

Solution A was prepared by dissolving 6.50 g ammonium molybdate, 6.61 g ammonium rhenate and 0.17 g silver acetate in 50 ml water heated to 70° C. Solution B was prepared by dissolving 3.01 g ammonium vanadate in 70 ml water heated to 70° C. Solution C was prepared by dissolving 1.89 g niobium chloride, 0.88 g antimony acetate, 0.32 g calcium nitrate and 2.24 g oxalic acid in 50 ml water heated to 70° C. The rest of the procedure was as in comparative example A. The nominal composition of the catalyst was thus $Mo_{1.00}Re_{0.69}V_{0.72}Nb_{0.25}Sb_{0.08}Ca_{0.03}Ag_{0.028}O_y$).

Example II ($Mo_{1.00}Re_{0.69}V_{0.72}Nb_{0.25}Sb_{0.08}Ca_{0.03}Ir_{0.028}O_y$)

Solution A was prepared by dissolving 6.50 g ammonium molybdate, 6.61 g ammonium rhenate and 0.49 g ammonium iridium hexachloride in 50 ml water heated to 70° C. Solution B was prepared by dissolving 3.01 g ammonium vanadate in 70 ml water heated to 70° C. Solution C was prepared by dissolving 1.89 g niobium chloride, 0.88 g antimony acetate, 0.32 g calcium nitrate and 2.24 g oxalic acid in 50 ml water heated to 70° C. The rest of the procedure was as in comparative example A. The nominal composition of the catalyst was thus $Mo_{1.00}Re_{0.69}V_{0.72}Nb_{0.25}Sb_{0.08}Ca_{0.03}Ir_{0.028}O_y$.

Example III ($Mo_{1.00}V_{0.25}Nb_{0.12}Ag_{0.014}O_y$.)

As for example A except that 0.17 g Ag acetate was added in the preparation of solution A. The nominal composition of the catalyst was thus $Mo_{1.00}V_{0.25}Nb_{0.12}Ag_{0.014}O_y$.

Example IV
($Mo_{1.00}V_{0.25}Nb_{0.12}Ag_{0.000028}Ir_{0.0000018}O_y$.)

As for example A. Subsequent analysis revealed the presence of amounts of silver and iridium equivalent to 0.00036 g Ag acetate and 0.0000013 g ammonium Ir chloride in the preparation. The composition of the catalyst was thus $Mo_{1.00}V_{0.25}Nb_{0.12}Ag_{0.000028}Ir_{0.0000018}O_y$.

CATALYST TEST PROCEDURE

Typically 5 mls of catalyst were loaded into a fixed bed reactor made of Hasetelloy grade C276 of dimensions 12 mm internal diameter and length 40 cm. Glass beads were used to maintain the catalyst in position in the centre of the reactor. Above the catalyst the glass beads thus acted as a mixing and pre-heating zone for gaseous and liquid reagents. The test apparatus was then pressure-tested at 21 bar with helium to check for leaks. Catalysts were then activated by heating to 220° C. at 5° C./min in helium at 21 bar for 16 hours, to ensure full decomposition of catalyst precursors.

The required flows of ethane, 20% oxygen in helium and water were then introduced to the reactor, to ensure an inlet composition of 42% v/v ethane, 6.6% v/v oxygen, 25% v/v helium and 26.4% v/v water (as steam). The total feed flow rate was maintained at a level to ensure a feed GHSV of 2970/h. After equilibrating for 30 minutes, gas samples were taken from the outlet stream to calibrate a GC (model Unicam 4400) for ethane, oxygen and helium. Next, the setpoint temperature of the reactor was increased until typically 75% oxygen conversion was achieved, as indicated by the presence in the outlet stream of 2.2% v/v oxygen.

Following an equilibration period of 30 minutes, catalysts were then evaluated under steady state conditions for a period of typically 4–5 hours. Exit gas volume was measured over the ran period by a water-gas meter. Liquid products were collected and weighed after the run period. Composition of gas and liquid products was measured using GC analysis (Unicam 4400 and 4200 fitted with TCD and FID detectors respectively).

All feed and product flow rates and compositions were entered into an Excel spreadsheet, and the following parameters calculated:

ethane conversion (cnv)=(inlet mol ethane−outlet mol ethane)/inlet mol ethane×100 oxygen conversion (cnv)=(inlet mol oxygen−outlet mol oxygen)/inlet mol oxygen×100 selectivity to AcOH (C-mol %)=(outlet mol AcOH×2)/(mol ethane converted×2)×100 selectivity to ethylene (C-mol %)=(outlet mol ethylene×2)/(mol ethane converted×2)×100 selectivity to CO(C-mol %)=(outlet mol CO)/(mol ethane converted×2)×100 selectivity to $CO_2$ (C-mol %)=(outlet mol $CO_2$)/(mol ethane converted×2)×100 selectivity to $CO_x$ (C-mol %)=selectivity to CO+selectivity to $CO_2$

STY (space time yield)%=(g AcOH)/liter catalyst bed/hour

Typically, mass balance and carbon balance for a reaction was found to be 100+/−5%.

Catalyst Comparisons

The following table compares the catalyst performance of the above-described catalysts. Each catalyst was evaluated under standard conditions indicated in the table, except for the temperature, which was varied so as to achieve 70–90% oxygen conversion, in order to facilitate comparison.

The data in the table illustrates clearly the promotional effect of Ag, Ir and Ag—Ir on Mo—V—Nb based oxide catalysts. Thus, the data in the table clearly illustrate that Ag-promoted catalyst (catalyst I) performs better than unpromoted catalyst (F) in terms of high acetic acid selectivity and low carbon oxides selectivity. In addition, the data indicate that Ir-promoted catalyst (II) is superior to unpromoted catalyst (F) in terms of higher acetic acid selectivity.

On the basis of these results, Ag and Ir are also both effective catalyst promoters for ethane oxidation to acetic acid in the absence of a Pd promoter.

| Example/Comparative Example | Catalyst Composition | Tset °C. | Tbed °C. | Ethane cnv % | Oxygen cnv % | $S(C_2H_4)$ % C-mol | $S(CO_x)$ % C-mol | S(AcOH) % C-mol | STY AcOH g/l-cat/h |
|---|---|---|---|---|---|---|---|---|---|
| A | $Mo_{1.00}V_{0.25}Nb_{0.12}$ | | 326 | 3.2 | 82.4 | 41.9 | 16.2 | 41.3 | 82.0 |
| B | $Mo_{1.00}V_{0.25}$ | | 314 | 4.8 | 79.4 | 15.1 | 67.0 | 17.8 | 19.7 |
| C | $Mo_{1.00}V_{0.25}Nb_{0.12}Pd_{0.014}$ | | 253 | 3.9 | 76.8 | 0.0 | 36.9 | 62.9 | 82.4 |
| D | $Mo_{1.00}V_{0.25}Nb_{0.12}Ru_{0.014}$ | | 293 | 5.0 | 71.8 | 43.7 | 16.5 | 39.8 | 70.2 |
| E | $Mo_{1.00}V_{0.25}Nb_{0.12}Rh_{0.014}$ | | 304 | 5.7 | 87.5 | 43.1 | 15.5 | 40.3 | 89.3 |

-continued

| Example/ Comparative Example | Catalyst Composition | Tset °C. | Tbed °C. | Ethane cnv % | Oxygen cnv % | S(C$_2$H$_4$) % C-mol | S(CO$_x$) % C-mol | S(AcOH) % C-mol | STY AcOH g/l-cat/h |
|---|---|---|---|---|---|---|---|---|---|
| F | Mo$_{1.00}$Re$_{0.69}$V$_{0.72}$Nb$_{0.25}$Sb$_{0.08}$Ca$_{0.03}$ | 300 | 309 | 5.7 | 75.1 | 26.3 | 22.7 | 50.4 | 126.0 |
| G | Mo$_{1.00}$Re$_{0.69}$V$_{0.72}$Nb$_{0.25}$Sb$_{0.08}$Ca$_{0.04}$Pd$_{0.011}$ | | 286 | 6.2 | 73.0 | 14.8 | 8.2 | 76.5 | 187.8 |
| I | Mo$_{1.00}$Re$_{0.69}$V$_{0.72}$Nb$_{0.25}$Sb$_{0.08}$Ca$_{0.04}$Ag$_{0.028}$ | 250 | 262 | 5.7 | 75.0 | 19.3 | 3.6 | 76.2 | 183.3 |
| II | Mo$_{1.00}$Re$_{0.69}$V$_{0.72}$Nb$_{0.25}$Sb$_{0.08}$Ca$_{0.04}$Ir$_{0.028}$ | 230 | 243 | 2.6 | 57.2 | 33.9 | 3.0 | 63.0 | 81.9 |
| II | Mo$_{1.00}$Re$_{0.69}$V$_{0.72}$Nb$_{0.25}$Sb$_{0.08}$Ca$_{0.04}$Ir$_{0.028}$ | 280 | 308 | 5.3 | 98.8 | 20.1 | 20.8 | 59.1 | 131.9 |
| III | Mo$_{1.00}$V$_{0.25}$Nb$_{0.12}$Sb$_{0.08}$Ag$_{0.014}$ | 280 | 296 | 3.4 | 74.9 | 33.9 | 7.2 | 59.0 | 100.0 |
| IV | Mo$_{1.00}$V$_{0.25}$Nb$_{0.12}$Ag$_{0.000028}$Ir$_{0.0000018}$ | | 296 | 4.1 | 77.1 | 28.2 | 6.8 | 65.1 | 124.9 |

Conditions: 21 bar, 42% v/v ethane, 6.6% oxygen, 25% water, GHSV = 2970

We claim:

1. A catalyst composition comprising in combination with oxygen the elements:

$$Mo_a.W_b.Ag_c.Ir_d.X_e.Y_f \quad (I)$$

wherein X is the elements Nb and V;

Y is one or more elements selected from the group consisting of:
Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd;

a, b, c, d, e and f represent the gram atom ratios of the elements such that
$0 < a \leq 1$, $0 \leq b < 1$ and $a+b=1$;
$0 < (c+d) \leq 0.1$;
$0 < e \leq 2$; and
$0 \leq f \leq 2$.

2. A catalyst composition as claimed in claim 1 in which c and d are such that c+d is at least $10^{-6}$.

3. A catalyst composition as claimed in claim 2 in which c and d are such that $(c+d) \leq 0.05$.

4. A catalyst composition as claimed in claim 1, 2 or 3 in which more silver is present than iridium on a gram atom basis.

5. A catalyst composition as claimed in claim 4 in which c is at least 10 times d.

6. A catalyst composition as claimed in claim 1 in which e is at least 0.05.

7. A catalyst composition as claimed in claim 6 in which e is no greater than 0.5.

8. A catalyst composition as claimed in claim 1 in which f is at least $10^{-6}$.

9. A catalyst composition as claimed in claim 8 in which f is no greater than 0.2.

10. A catalyst composition as claimed in claim 1 in which Y is at least one element selected from the group consisting of Cu, Pd, Pt, Re, Ru and Sb.

11. A catalyst composition as claimed in claim 1 in which a is at least 0.1.

12. A catalyst as claimed in claim 1 in which b is no greater than 0.9.

13. A catalyst composition as claimed in claim 1 in which formula (I) is selected from the group consisting of:

Mo$_a$.W$_b$.Ag$_c$.X$_e$.Y$_f$; Mo$_a$.W$_b$.Ir$_d$.X$_e$.Y$_f$; Mo$_a$.W$_{b \cdot c+d}$.X$_e$.Y$_f$; Mo$_a$.Ag$_c$.X$_e$.Y$_f$; Mo$_a$.Ir$_d$.X$_e$.Y$_f$; Mo$_a$._{c+d}$.X$_e$.Y$_f$; Mo$_{a+b}$.Ag$_c$.X$_e$.Y$_f$; $_{a+b}$.Ir$_d$.X$_e$.Y$_f$; $_{a+b \cdot c+d}$.X$_e$.Y$_f$, wherein X is the elements Nb and V and wherein Y and a, b, c, d, e, and f are as defined in claim 1.

14. A catalyst composition as claimed in claim 1 in which e is at least 0.2.

15. A catalyst composition as claimed in claim 1 in which a is at least 0.5.

16. A catalyst composition selected from the group consisting of:
Mo$_{1.00}$.Re$_{0.69}$.V$_{0.72}$.Nb$_{0.25}$.Sb$_{0.08}$.Ca$_{0.03}$.Ag$_{0.028}$O$_y$;
Mo$_{1.00}$.Re$_{0.69}$.V$_{0.72}$.Nb$_{0.25}$.Sb$_{0.08}$.Ca$_{0.03}$.Ir$_{0.028}$O$_y$;
Mo$_{1.00}$.V$_{0.25}$.Nb$_{0.12}$.Ag$_{0.014}$O$_y$; and
Mo$_{1.00}$.V$_{0.25}$.Nb$_{0.12}$.Ag$_{0.000028}$.Ir$_{0.00000018}$O$_y$
wherein y is a number which satisfies the valencies of the elements in the composition for oxygen.

17. A catalyst composition comprising in combination with oxygen the elements:

Mo$_a$.W$_b$.Ag$_c$.Ir$_d$.X$_e$.Y$_f$ wherein X is the elements Nb and V;

Y is one or more elements selected from the group consisting of:
Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd;

a, b, c, d, e and f represent the gram atom ratios of the elements such that
$0 < a \leq 1$, $0 \leq b < 1$ and $a+b=1$;
$0 < (c+d) \leq 0.1$;
$0.2 \leq e \leq 2$; and
$0 \leq f \leq 2$.

18. A catalyst composition as claimed in claim 17 in which c and d are such that c+d is at least $10^{-6}$.

19. A catalyst composition as claimed in claim 18 in which c and d are such that $(c+d) \leq 0.05$.

20. A catalyst composition as claimed in claim 17 in which more silver is present than iridium on a gram atom basis.

21. A catalyst composition as claimed in claim 20 in which c is at least 10 times d.

22. A catalyst composition as claimed in claim 17 in which e is no greater than 0.5.

23. A catalyst composition as claimed in claim 17 in which f is at least $10^{-6}$.

24. A catalyst composition as claimed in claim 23 in which f is no greater than 0.2.

25. A catalyst composition as claimed in claim 17 in which Y is at least one element selected from the group consisting of Cu, Pd, Pt, Re, Ru and Sb.

26. A catalyst composition as claimed in claim 17 in which a is at least 0.1.

27. A catalyst as claimed in claim 17 in which b is no greater than 0.9.

28. A catalyst composition as claimed in claim 17 in which formula (I) is selected from the group consisting of:

Mo$_a$.W$_b$.Ag$_c$.X$_e$.Y$_f$; Mo$_a$.W$_b$.Ir$_d$.X$_e$.Y$_f$; Mo$_a$.W$_{b \cdot c+d}$.X$_e$.Y$_f$; Mo$_a$.Ag$_c$.X$_e$.Y$_f$; Mo$_a$.Ir$_d$.X$_e$.Y$_f$; Mo$_a$._{c+d}$.X$_e$.Y$_f$; Mo$_{a+b}$.Ag$_c$.X$_e$.Y$_f$; $_{a+b}$.Ir$_d$.X$_e$.Y$_f$; $_{a+b \cdot c+d}$.X$_e$.Y$_f$, wherein X is the elements Nb and V and wherein Y and a, b, c, d, e, and f are as defined in claim 17.

29. A catalyst composition as claimed in claim 17 in which a is at least 0.5.

* * * * *